United States Patent [19]

Sorenson

[11] Patent Number: 4,657,928
[45] Date of Patent: Apr. 14, 1987

[54] ORGANIC COPPER COMPLEXES AS RADIOPROTECTANTS

[75] Inventor: John R. J. Sorenson, Little Rock, Ark.

[73] Assignee: International Copper Research Association, Inc., New York, N.Y.

[21] Appl. No.: 654,086

[22] Filed: Sep. 25, 1984

Related U.S. Application Data

[63] Continuation-in-part of Ser. No. 382,557, May 27, 1982, abandoned.

[51] Int. Cl.$^4$ .......................... C07F 1/08; A01N 55/02; A61K 31/30
[52] U.S. Cl. .................................. 514/499; 556/115; 556/116; 514/500
[58] Field of Search .......................................... 514/499

[56] References Cited

U.S. PATENT DOCUMENTS

| | | | |
|---|---|---|---|
| 3,884,949 | 5/1975 | Eicke et al. | 260/438.1 X |
| 4,221,785 | 9/1980 | Sorenson | 424/230 |
| 4,287,190 | 9/1981 | Boettcher et al. | 260/438.1 X |
| 4,373,953 | 2/1983 | Deinet et al. | 424/294 X |

OTHER PUBLICATIONS

Chemical Abstracts 69 113013z (1968).
Chemical Abstracts 84 38591r (1976).
Chemical Abstracts 85 116777t (1976).
Leuthauser, Antitumor Activities of Superoxide Dismutase and Copper Coordination Compounds, Ph.D. Thesis Iowa City, University of Iowa (1979).
Beauchamp et al, Anal. Biochem. 44 276–287 (1971).
Sorenson, J. Med. Chem. 19 135–148 (1976).
Georgieff, Science 173 537–539 (1971).
Sorenson, Inflammation 1 317–331 (1976).
Leuthauser et al, J. Nat'l Cancer Inst. 66 1077–1081 (1981).
Westman et al, Cancer Res. 41 2962–2966 (1981).
Oberley et al, Cancer Res. 39 1141–1149 (1979).

Primary Examiner—Helen M. S. Sneed
Attorney, Agent, or Firm—Pennie & Edmonds

[57] ABSTRACT

Methods are described for using organic copper complexes or their solvates, which exhibit superoxide dismutase activity and act as superoxide radical scavengers, as radioprotectants to protect mammalian cells from damage caused by gamma- or x-irradiation. Treatment can result in the protection of normal tissues in cancer patients undergoing radiotherapy and in the protection of individuals who may be at risk with regard to hazardous effects of exposure to occupational or environmental ionizing radiation.

37 Claims, 1 Drawing Figure

ORGANIC COPPER COMPLEXES AS RADIOPROTECTANTS

This application is a continuation-in-part of copending U.S. application Ser. No. 382,557, filed May 27, 1982, now abandoned which is incorporated by reference herein.

FIELD OF THE INVENTION

The present invention relates to methods for providing radioprotection using certain organic copper complexes. While this invention is not to be construed as limited to any particular mode of action of such copper complexes, it is believed that they provide radioprotection by virtue of their superoxide dismutase mimetic activity and act as superoxide radical scavengers to protect mammalian cells from damage caused by gamma-rays or X-rays. Treatment can result in the protection of normal tissues in cancer patients undergoing radiotherapy and protection of individuals who may be at risk with regard to hazardous effects of exposure to ionizing radiation.

BACKGROUND OF THE INVENTION

It is now understood that oxygenated aqueous solutions exposed to high energy gamma- or X-rays yield radiolytic products according to the following reaction:

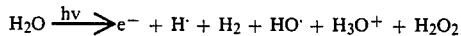

$$H_2O \xrightarrow{h\nu} e^- + H\cdot + H_2 + HO\cdot + H_3O^+ + H_2O_2$$

See, for example, Bors, et al., Curr. Top. Radiat. Res. 9:247 (1974). Energy-rich radicals, $H\cdot$ and $e_2^-$, lead to superoxide ($^-O\cdot O\cdot$ or $O_2^-$) formation at diffusion controlled rates (greater than $10^{10}M^{-1}s^{-1}$) in the presence of singlet or triplet state dioxygen according to the following reactions:

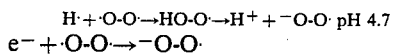

$$H\cdot + \cdot O\cdot O\cdot \rightarrow HO\cdot O\cdot \rightarrow H^+ + {}^-O\cdot O\cdot \quad pH\ 4.7$$
$$e^- + \cdot O\cdot O\cdot \rightarrow {}^-O\cdot O\cdot$$

See, Behar, et al., J. Phys. Chem. 74:3209 (1970); Czapski, Ann. Rev. Phys. Chem. 22:171 (1971); Thomas, In "Radiation Research", Silini (ed.), Elsevier/North-Holland: New York, 1967, p. 179. Formation of superoxide partially accounts for the well known oxygen enhancement of radiation-induced cell damage.

The enzyme superoxide dismutase (SOD) plays a significant role in the defense against oxygen toxicity in aerobic organisms. Superoxide dismutase catalyzes the dismutation of $O_2^-$, as follows:

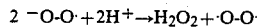

$$2\ {}^-O\cdot O\cdot + 2H^+ \rightarrow H_2O_2 + \cdot O\cdot O\cdot$$

See McCord, et al., J. Biol. Chem. 244:6049 (1969); Fridovich, Science 201:875 (1978). The rate of this reaction is also diffusion controlled, $k = 1.3 \times 10^9 M^{-1}s^{-1}$. Czapski, Ann. Rev. Phys. Chem. 22:71 (1971).

In a mammalian cell, two types of SOD are found. One contains both copper and zinc and is located in the cytosol and periplasmic space of the mitochondria (Cu-Zn SOD). The other enzyme contains manganese and is present in the matrix of the mitochondria (MnSOD). All normal mammalian cell types investigated contain these two types of the enzyme, except erythrocytes which lack MnSOD.

The specificity with which Cu-Zn SOD catalyzes the destruction of superoxide, together with the demonstrated radioprotection of enzymes, bacteriophage, bacteria, mycoplasma, and mammalian cells with Cu-Zn SOD, has prompted the examination of the prophylactic effect of Cu-Zn SOD on survival of whole-body 6.5 Gy (1 Gy=100 rads) x-irradiated mice. Petkau, et al., Biochem. Biophys. Res. Comm. 65:886 (1975); Petkau, et al., Biophys. Res. Comm. 67:1167 (1975); Petkau, et al., Int. J. Radiat. Biol. 29:297 (1976). The maximal effective dose of Cu-Zn SOD was 1.1 uM/kg. Higher and lower doses were less effective when the enzyme was given intravenously (iv) one hour prior to irradiation, the time at which maximum concentrations of $^{125}I$-labeled enzyme were found in bone marrow and bone marrow stem cells. Pretreatment with 1.1 uM/kg Cu-Zn SOD increased the $LD_{50/30}$ dose of radiation from 6.3 Gy to 7.0 Gy and 10 percent survival was observed with a $LD_{100/30}$ dose of radiation, 8.2 Gy. The same dose of Cu-Zn SOD given 1 hour before and 1 hour after irradiation further increased the $LD_{50/30}$ dose to 8.7 Gy and 17% of the mice survived when the radiation dose was increased to 10 Gy.

These results are consistent with the recognized normal biochemical role of Cu-Zn SOD and have been interpreted as explaining the well known "oxygen effect", the increase in radiation sensitivity associated with the presence of oxygen and the decrease in radiation sensitivity in the absence of oxygen.

Effective and less toxic radioprotectants are needed for protection of normal tissues of patients undergoing radiation therapy for neoplastic disease. The most effective radioprotectant developed to date, S-2-(3-aminopropylamino) ethyl-phosphorothioic acid (WR2721), produces a number of undesirable side effects. Ongoing clinical trials have been complicated by emesis, hypertension, hypotension, somnolence and allergy. Kligerman, et al., First Conference on Radioprotectors and Anticarcinogens, National Bureau of Standards, Gaithersburg, Maryland, June 21-24 (1982); Glick, et al., First Conference on Radioprotectors and Anticarcinogens, National Bureau of Standards, Gaithersburg, Maryland, June 21-24 (1982).

Concentrations of plasma copper complexes are known to increase in neoplastic disease states and to return to normal during remission. Sorenson, In "Copper Complexes in the Environment, Part II Health Effects", Niragu (ed.) John Wiley and Sons, New York, 1979, p. 83. Since copper complexes have antineoplastic, anticarcinogenic and antimutagenic effects, and since such complexes decrease in plasma concentration during remission, they may be a component of physiologic responses which facilitate remission.

SUMMARY OF THE INVENTION

The present invention involves the use of certain organic copper complexes with superoxide dismutase mimetic activity as radioprotectants. The use of copper complexes can also provide a range of pharmacological effects including anticancer, antimutagenic and anticarcinogenic effects. As radioprotectants, the complexes have the ability to protect animals and human beings against the adverse toxic effects of superoxide formation resulting from exposure to gamma-rays or x-rays. In particular, certain copper salicylate and acetylsalicylate complexes, their solvates, as well as mixtures thereof, are useful in protecting against such superoxide toxic effects.

More specifically, copper 3,5-diisopropylsalicylate [Cu(II)(3,5-dips)$_2$] and other copper complexes, such as Cu(II)(salicylate)$_2$, Cu(II)(3,5-ditertiarybutylsalicylate)$_2$, Cu(II)$_2$(acetylsalicylate)$_4$, Cu(II)$_2$(acetylsalicylate)$_4$(dimethylsulfoxide)$_4$, and Cu(II)$_2$(acetylsalicylate)$_4$(pyridine)$_4$ are superoxide scavengers and have molecular weights that enable penetration into cell membranes. Of the salicylate complexes, molecular weights are between about 340 and about 1000, preferably between about 340 and about 600, and for the acetylsalicylate complexes, the molecular weights are between about 845 and about 1800, preferably between about 845 and about 1400. Additionally, the copper complexes, specifically Cu(II)(3,5-dips)$_2$, are lipid soluble (soluble in diethylether) and capable of crossing lipid membranes. Thus, these copper complexes with their low molecular weights, and their lipid solubility, allow for excellent penetration of cell membranes, mitochondrial membranes and organelles. See Leuthauser, et al., Antitumor Effect of a Copper Coordination Compound With Superoxide Dismutase-Like Activity, J. Natl. Cancer Inst. 66:1077 (1981), hereby incorporated by reference. It is to be noted that native SOD has a molecular weight of about 32,000 daltons and, as a result, does not penetrate well into cell membranes.

Thus, as demonstrated hereafter, the above noted organic copper complexes, as well as other organic copper complexes having superoxide scavenging ability, and mixtures thereof, can be advantageously used to protect against superoxide damage from radiation of human and animal tissues, for example, radiation treatment of neoplasms.

Copper complexes also offer protection against the effects of recurrent occupational or environmental exposure to ionizing radiation or accidental nonrecurrent total-body exposures to doses of ionizing radiation that are larger than those used to therapeutically irradiate neoplasms. Accidental exposure to doses of radiation, for example in the range of 2 to 10 Gy, produces lethal immunoincompetence due to suppression of bone marrow stem cell division and inflammation (hematopoietic syndrome). Larger doses of irradiation, for example in the range of 10 to 50 Gy, produce immunoincompetence, inflammation and gastric ulceration (gastrointestinal syndrome). Still larger doses, for example in the range of 50 to 100 Gy, produce, in addition to symptoms of hematopoietic and gastrointestinal syndromes, damage to the central nervous system leading to tremors and convulsions prior to death (central nervous system syndrome). Many copper complexes, including Cu(II)(3,5-dips)$_2$, have been shown to have anti-inflammatory activity and to promote wound healing. Such properties, in conjunction with superoxide scavenging ability, are highly desirable in protecting against the hematopoietic, gastrointestinal and central nervous system syndrome induced by progressively increasing doses of ionizing radiation.

The organic copper complexes described herein may be administered, orally, topically, rectally or parenterally (intramuscularly, intraperitoneally or intravenously), within about two weeks before or after exposure of the human being or animal to gamma-rays or X-rays. Appropriate dosage concentrations and regimens that would be therapeutically effective, as well as appropriate pharmaceutical carriers, are obtainable by routine experimentation by one of ordinary skill.

While it has not been possible to definitively prove the precise mechanism by which the copper complexes of the invention exert their radioprotectant effect, knowledge of such mechanism is not crucial to the practice of this invention. The discussion herein merely discusses the proposed mechanism believed to be involved in the radioprotectant effect observed.

BRIEF DESCRIPTION OF THE FIGURE

The invention may be more fully understood by reference to the data presented in the appended drawing sheet in which.

DETAILED DESCRIPTION OF THE INVENTION

Figure 1:
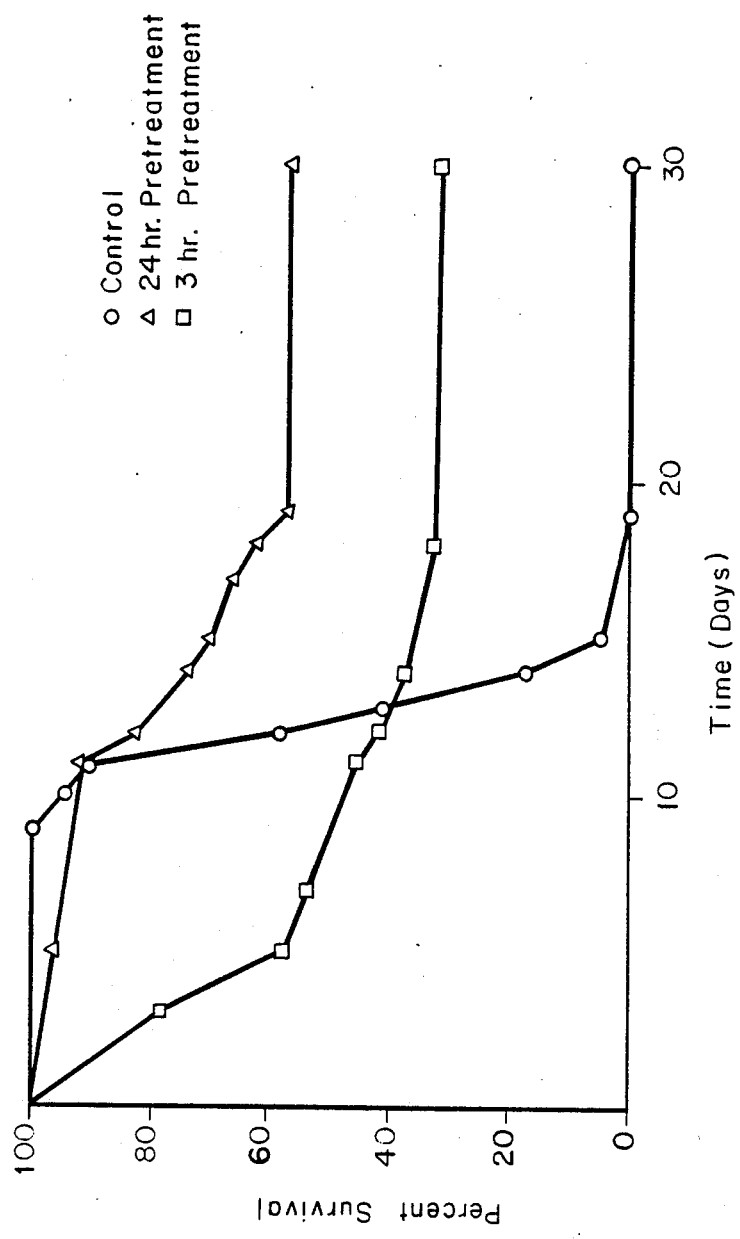
FIG. 1 depicts the survival over time of lethally irradiated mice treated with Cu(II)(3,5-dips)$_2$.

This invention relates to the use of certain organic copper complexes having superoxide dismutase activity as radioprotectants. These complexes may be used therapeutically for the protection of normal tissues during cancer radiotherapy, or for treatment immediately after accidental exposure to harmful doses of radiation. They may also be used prophylatically for protection against occupational or environmental exposures to hazardous radiation. More specifically, the use of copper salicylate and acetylsalicylate complexes, and in particular Cu(II)(3,5-dips)$_2$, as radioprotectants is described.

As set forth above, it is believed that certain organic copper salicylate and acetylsalicylate complexes provide protection for the host animal against lethal doses of radiation by catalyzing the disproportionation of superoxide formed in the tissues by irradiation. Moreover, since the complexes are lipid soluble, they are capable of crossing lipid membrane barriers and scavenging superoxide formed within cells.

The particular embodiment described in complete detail herein concerns the use of Cu(II)(3,5-dips)$_2$. This compound has an LD$_{50/7}$ in mice of at least 280 mg/kg and 240 mg/kg in rats (following subcutaneous injection). By extrapolation, assuming comparable pharmacokinetics and toxicological response, the predicted LD$_{50}$ in human beings would be approximately 250 mg/kg of body weight. A minimum prophylatic dose would be about 0.001 mg/kg, while a therapeutic dose would range from about 1 mg to 100 mg/kg, depending upon the radiation dose. Therapeutic doses would be initiated about two weeks before radiotherapy, and would continue as necessary after the radiation treatment. For cases of accidental exposure, treatment would be initiated immediately after exposure and continued as necessary thereafter. Prophylactic doses would be taken on a continuing basis, for example a daily basis, as long as the recurrent radiation exposure continued. In any of these cases, the route of administration might be oral, topical, rectal or parenteral (e.g., intramuscular, intravenous, subcutaneous, or intraperitoneal).

The organic copper complex can be combined with either a liquid or solid pharmaceutical carrier and could take the from of capsules, tablets, powders, granules, suspensions or solutions.

It should be noted, however, that the process described herein is not limited to the use of Cu(II)(3,5-dips)$_2$ and may be used for any suitable organic copper complex having superoxide dismutase activity, and especially the copper salicylates and acetylsalicylates, such as Cu(II)(salicylate)$_2$, Cu(II)(3,5-ditertiarybutylsalicylate)$_2$, Cu(II)$_2$(acetylsalicylate)$_2$, and their solvates such as Cu(II)$_2$(acetylsalicylate)$_4$(dimethylsulfoxide)$_4$ and Cu(II)$_2$(acetylsalicylate)$_4$(pyridine)$_4$.

Other organic copper complexes that are normal constituents of serum or plasma also have radioprotectant capability. These complexes, which increase in concentration in response to tissue irritation or damage (Michelson et al., In "Superoxide and Superoxide Dismutases," Michelson et al. (eds.), Academic Press, New York, 1977, p. 467), include Cu(II)(histidinate)(cystinate), Cu(II)(histidinate)(cystinate H), Cu(II)(histidinate)$_2$, Cu(II)(histidinate)(threoninate), Cu(II)(histidinate)(valinate), Cu(II)(histidinate)(lysinate), Cu(II)(histidinate)(alaninate), Cu(II)(histidinate)(serinate), Cu(II)(histidinate)(pnenylalaninate) and Cu(II)(histidinate)(glycinate).

The copper complexes of recognized radioprotectants, which have been reviewed by Prasad, In "Radiation Biology," Pizzarello and Colombetti (eds.), C.R.C. Press Inc., Boca Raton, 1982, p. 205, also have radioprotectant capability. These complexes include Cu(I)$_n$-(cysteinate)$_n$ polymeric, Cu(I)(2-aminoetnylthiolate), Cu(II)(cystamine)$_2$++, Cu(II)(aminoethylisothiourea)$_2$, Cu(I)(2-guanidinoethylthiolate), Cu(I)[N-(3-aminopropyl)2-aminothiolate], Cu(I)(isothiourea), Cu(II)[N-(3-aminopropyl)-2-aminoethylthiophosphate], Cu(I)(uracilthiolate), Cu(I)(isothiocarbamate) and Cu(I)(thioamidoisothiamide).

The superoxide dismutase activities of certain of tnese copper complexes are listed in Table I.

TABLE I

SOD-like Activity, Percent Reactivity, and Rate of Superoxide Dismutation for Some Copper Salicylates and Cu—Zn SOD

| Complex or Enzyme | Concentration (uM)* | Percent Reactivity | Rate ($\times 10 \, M^{-1}s^{-1}$) |
| --- | --- | --- | --- |
| Cu—Zn SOD | 0.02 | 100 | 1.3** |
| Cu(II) (3,5-dips)$_2$ | 2.9 | 0.70 | 1-2 |
| Cu(II) (salicylate)$_2$ | 4.6 | 0.65 | 1.6** |
| Cu(II)$_2$—(acetylsalicylate)$_4$ | 3.1 | 0.043 | N.D*** |
| Cu(II)$_2$—(acetylsalicylate)$_4$-(DMSO)$_2$ | 2.8 | 0.69 | N.D. |
| Cu(II)$_2$—(acetylsalicylate)$_4$-(pyridine)$_2$ | 2.7 | 0.32 | N.D. |
| Cu(II) (3,5-ditertiary-butylsalicylate)$_2$ | 6.2 | 0.74 | N.D. |

*Compound required for 50% inhibition of superoxide reduction of nitroblue tetrazolium.
**Weser, et al., In "Inflammatory Diseases and Copper", Sorenson (ed.), Humana Press: Clifton, New Jersey (1982), p. 513
***N.D. = Not Determined EXAMPLE: RADIOPROTECTANT EFFECT OF COPPER 3,5-DIISOPROPYLSALICYLATE Cu(II)(3,5-dips)$_2$ AND COMPOSITIONS THEREOF Copper 3,5-diisopropylsalicylate was synthesized according to the method of Sorenson, J. Med. Chem. 19:135 (1976), which is incorporated herein by reference. Cu(II)(3,5-dips)$_2$ is lipid soluble, and the LD50 is 240 +33 mg/kg when administered subcutaneously to rats.

To measure SOD activity, the method of Beauchamp and Fridovich (Anal. Biochem. 44:276 (1971)) was used. Dimethyl sulfoxide (DMSO) solvated superoxide (KO$_2$) and the xanthine-xanthine oxidase methods were used to generate O$_2^-$. Cu(II)(3,5-dips)$_2$ is dissolved in DMSO. This modified method was chosen due to the lipid solubility of Cu(II)(3,5-dips)$_2$ and the solvating character of DMSO. Free O$_2^-$ is released when DMSO-KO$_2$ is added to an aqueous solution. Reaction mixtures contained 1:20 dilution of a saturated KO$_2$ solution (20 mg KO$_2$/ml of dimethyl sulfoxide), $5.6 \times 10^{-5}$M of nitroblue tetrazolium, 1 unit of catalase and 0-500 ug of Cu(II)(3,5-dips)$_2$ in 0.5 M potassium phosphate buffer, pH 7.8. The formation of blue formazan is determined by recording the final absorbance of the assay mixture at 560 nm. The sensitivity of this assay was found to be 0.85 ug of pure bovine SOD per unit of activity.

Using this modified assay method, Cu(II)(3,5-dips)$_2$ has a mean activity of 17,400±1,800 units per milligram.

A preferred solution for parenteral administration contains Cu(II)(3,5-dips)$_2$ in a sterile pyrogen-free saline solution containing either 0.25% Tween 80 (polyoxyethylene sorbitan monooleate) or 4% propylene glycol and 1.4% polyvinyl alcohol.

EXPERIMENTAL

One group of 22-control and two groups of 24-treated 8 to 10 week old female B6CBF1 mice (Cumberland View Farms, Clinton, Tennessee) were used. Control animals were given a subcutaneous (sc) injection of 0.3 ml of vehicle (0.25% Tween 80 in 0.9% pyrogen-free sterile saline) 24 hours before irradiation. One treatment group was given a single sc injection of 0.49 mM/kg of Cu(II)(3,5-dips)$_2$ in 0.3 ml of vehicle 3 hours before irradiation and the other group was given the same treatment 24 hours before irradiation.

Control and treated mice were placed in plexiglass cages and irradiated bilaterally with a $^{60}$Co source at a rate of 0.4±0.004 Gy per minute for 25 minutes to deliver a projected LD$_{100/30}$ dose of 10±0.1 Gy. This radiation dose was measured with an electrometer connected to 0.05 ml NBS calibrated ion chambers positioned inside wax phantom mice placed in plexiglass cages. The tissue to air ratio for these phantom mice has been determined to be 97 percent. Control and treated mice were housed 5 mice per cage and fed mouse chow and water ad libitum for the 30 day observation period.

Results presented in FIG. 1 show that Cu(II)(3,5-dips)$_2$ is an effective radioprotectant. Thirty-three percent (8 mice) of the mice treated 3 hours before irradiation survived and none died after day 18 post-irradiation. Fifty-eight percent (14 mice) of the mice treated 24 hours before irradiation survived and none died after day 19 post-irradiation. All of the control mice died by day 18 post-irradiation. When similarly treated mice were irradiated with 12 Gy there were no survivors.

While conditions under which the present data were obtained with Cu(II)(3,5-dips)$_2$ were different from those used by Petkau and his colleagues to determine the radioprotectant activity of Cu-Zn SOD, a comparison of these data suggest that Cu(II)(3,5-dips)$_2$ has the potential of being much more effective than Cu-Zn SOD. Cu(II)(3,5-dips)$_2$ produced much greater protection, 33% or 58% survival depending on the pretreatment interval, than Cu-Zn SOD.

Greater protection with Cu(II)(3,5-dips)$_2$, as compared to CU-Zn SOD, may not be attributed to superoxide disproportionation alone. Data presented in Table I, supra, show that Cu(II)(3,5-dips)$_2$ is not as efficient as Cu-Zn SOD in disproportionating superoxide although the kinetics of disproportionation by copper salicylates suggest equivalent diffusion-controlled disproportionation at the active copper site.

Smaller molecular size and lipophilicity of Cu-(II)(3,5-dips)$_2$ may, however, facilitate tissue distribution and cellular membrane transport, which is not possible for Cu-Zn SOD. The large molecular size of Cu-Zn SOD and its anionic character prevent its transport across cell membranes and, as a result, its protective effect can only be exerted in the extracellular spaces.

In addition to reacting with superoxide, small molecular weight copper complexes are known to react with hydroxyl radicals, electrons, and hydrogen atoms at rates which are also diffusion controlled, as shown in Table II. Hydroxyl radicals, energetic electrons, and hydrogen atoms would be expected to destroy Cu-Zn SOD by reacting with the protein of the enzyme before it reached the copper-dependent active site. In summary, lipophilicity and reaction with superoxide, hydroxyl radicals, electrons and hydrogen atoms may account for the greater radioprotectant activity of Cu-(II)(3,5-dips)$_2$ and other copper complexes of this invention.

TABLE II

Reaction Rates for Cupric Complexes with Hydroxyl Radicals Hydrated High Energy Electrons, and Hydrogen Atoms*

| Ligand | pH | Rate ($\times 10^9 M^{-1}s^{-1}$) |
|---|---|---|
| Cu(II) (L)$_2$ + HO· → Cu(III) (L)$_2$ + HO$^-$ | | |
| H$_2$O | 7.0 | 0.35 |
| H$_2$NCH$_2$CH$_2$NH$_2$ | 6.5 | 3.0–0.6 |
| H$_2$NCH$_2$CO$_2$ | 6.1 | 1.5–0.3 |
| CH$_3$CH(NH$_2$)CO$_2$ | 6.3 | 1.4–0.3 |
| H$_2$NCH$_2$CH$_2$CO$_2$ | 5.8 | 1.2–0.2 |
| CH$_3$CH$_2$CH(NH$_2$)CO$_2$ | 6.1 | 2.0–0.4 |
| CH$_3$CH$_2$CH(NH$_2$)CH$_2$CO$_2$ | 6.0 | 1.2–0.2 |
| NH$_2$CH$_2$CH$_2$CH$_2$CO$_2$ | 4.8 | 1.1–0.2 |
| Na$_2$EDTA | 7.0 | 4 |
| Cu(II) (L)$_2$ + e$^-_{aq}$ → Cu(I) (L)$_2$ | | |
| H$_2$O | 7 | 30 |
| Na$_2$EDTA | 12 | 10 |
| Cu(II) (L)$_2$ + H· → Cu(I) (L)$_2$ + H$^+$ | | |
| H$_2$O | 7 | 0.06–0.6 |

*Farhatziz, "Selected Specific Rates of Reactions of Transients from Water in Aqueous Solution", U.S. Government Printing Office, Washington, D.C., 1977.

All of the organic copper complexes described herein exhibit the superoxide scavenging ability of Cu(II)(3,5-dips)$_2$ and would therefore be expected to exhibit radioprotectant activity by protecting mammalian cells from damage caused by high energy gamma-rays and/or X-rays. Differences in the level of radioprotection would be expected for different copper complexes owing to differences in molecular weight, ability to penetrate cell membranes, and superoxide dismutase mimetic activity.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

What is claimed is:

1. A method of providing radioprotection, comprising: administering a radioprotective amount of an organic copper complex, or a solvate thereof, having superoxide dismutase activity to a human being or animal within about two weeks of exposing said human being or animal to therapeutic doses of gamma-rays or X-rays.

2. A method of providing radioprotection, comprising: periodically administering a radioprotective amount of an organic copper complex, or a solvate thereof, having superoxide dismutase activity to a human being to protect against recurrent occupational or environmental exposure to gamma-rays or X-rays.

3. The method according to claim 1 or 2, wherein the copper complex, or a solvate thereof, is a copper salicylate complex, or a solvate thereof.

4. The method according to claim 1 or 2, wherein the copper salicylate complex is copper(II)(3,5-diisopropylsalicylate)$_2$.

5. The method according to claim 1 or 2, wherein the copper salicylate complex is copper(II)(salicylate)$_2$.

6. The method according to claim 1 or 2, wherein the copper salicylate complex is copper(II)(3,5-ditertiarybutylsalicylate)$_2$.

7. The method according to claim 1 or 2, wherein the copper complex is a copper acetylsalicylate complex.

8. The method according to claim 1 or 2, wherein the copper complex is copper(II)$_2$(acetylsalicylate)$_2$.

9. The method according to claim 1 or 2, wherein the copper complex solvate is copper(II)$_2$(acetylsalicylate)$_4$(dimethylsulfoxide)$_4$.

10. The method according to claim 1 or 2, wherein the copper complex solvate is copper(II)$_2$(acetylsalicylate)$_4$(pyridine)$_4$.

11. The method according to claim 1 or 2, wherein the copper complex is Cu(II)(histidinate)(cystinate).

12. The method according to claim 1 or 2, wherein the copper complex is Cu(II)(histidinate)(cystinate H).

13. The method according to claim 1 or 2, wherein the copper complex is Cu(II)(histidinate)$_2$.

14. The method according to claim 1 or 2, wherein the copper complex is Cu(II)(histidinate)(threoninate).

15. The method according to claim 1 or 2, wherein the copper complex is Cu(II)(histidinate)(valinate).

16. The method according to claim 1 or 2, wherein the copper complex is Cu(II)(histidinate)(lysinate).

17. The method according to claim 1 or 2, wherein the copper complex is Cu(II)(histidinate)(alaninate).

18. The method according to claim 1 or 2, wherein the copper complex is Cu(II)(histidinate)(serinate).

19. The method according to claim 1 or 2, wherein the copper complex is Cu(II)(histidinate)(phenylalaninate).

20. The method according to claim 1 or 2, wherein the copper complex is Cu(II)(histidinate)(glycinate).

21. The method according to claim 1 or 2, wherein the copper complex is Cu(I)$_n$ (cysteinate)$_n$polymeric.

22. The method according to claim 1 or 2, wherein the copper complex is Cu(I)(2-aminoethylthiolate).

23. The method according to claim 1 or 2, wherein the copper complex is Cu(II)(cystamine)$_2$++.

24. The method according to claim 1 or 2, wherein the copper complex is Cu(II)(aminoethylisothiourea)$_2$.

25. The method according to claim 1 or 2, wherein the copper complex is Cu(I)(2-guanidinoethylthiolate).

26. The method according to claim 1 or 2, wherein the copper complex is Cu(I).

27. The method according to claim 1 or 2, wherein the copper complex is Cu(II).

28. The method according to claim 1 or 2, wherein the copper complex is Cu(I)(isothiourea).

29. The method according to claim 1 or 2, wherein the copper complex is Cu(I)(uracilthiolate).

30. The method according to claim 1 or 2, wherein the copper complex is Cu(I)(isothiocarbamate).

31. The method according to claim 1 or 2, wherein the copper complex is Cu(I)(thioamidoisothiamide).

32. The method according to claim 1, wherein the copper complex, or solvate thereof, is administered before exposure to large doses of gamma-rays or X-rays.

33. The method according to claim 1, wherein the copper complex, or solvate thereof, is administered after exposure to large doses of gamma-rays or X-rays.

34. The method according to claim 1 or 2, wherein the copper complex, or solvate thereof, is administered subcutaneously.

35. The method according to claim 1 or 2, wherein the copper complex, or solvate thereof, is administered intravenously.

36. The method according to claim 1 or 2, wherein the copper complex, or solvate thereof, is administered orally.

37. The method according to claim 2, wherein the copper complex, or solvate thereof, is administered daily.

* * * * *